United States Patent [19]
Savidakis et al.

[11] Patent Number: 6,118,018
[45] Date of Patent: Sep. 12, 2000

[54] CHLORINATION AND BROMINATION OF AROMATIC COMPOUNDS AT ATMOSPHERIC PRESSURE

[75] Inventors: Michael C. Savidakis, Niagara Falls; Michael J. Fifolt, Grand Island; Daniel R. Thielen, Snyder; Ronald Spohn, Getzville; David C. Johnson, Cheektowaga; William S. Derwin, Grand Island, all of N.Y.

[73] Assignee: Occidental Chemical Corporation, Dallas, Tex.

[21] Appl. No.: 09/455,882

[22] Filed: Dec. 6, 1999

[51] Int. Cl.[7] .......................... C07C 69/76; C07C 255/00; C07C 17/00; C07C 45/00
[52] U.S. Cl. ........................ 560/103; 558/425; 568/323; 568/656; 570/206; 570/207; 570/210
[58] Field of Search ..................................... 570/206, 207, 570/210; 568/323, 656; 560/103; 558/425

[56] References Cited

U.S. PATENT DOCUMENTS 4,186,153  1/1980  Potts ........................................ 570/207

OTHER PUBLICATIONS

Roberts and Caserio, Basic Principles of Org Chem, Jan. 1964.

*Primary Examiner*—Alan Siegel
*Attorney, Agent, or Firm*—Anne E. Brookes; Richard D. Fuerle

[57] ABSTRACT

Disclosed is a method of adding 1 to 4 chlorine or bromine atoms to an aromatic ring of compound that has at least one electron-withdrawing groups on that ring. The aromatic compound is reacted with a chlorinating agent or a brominating agent in the presence of about 0.1 to about 10 mole % of a Lewis acid catalyst and about 0.001 to about 0.1 equivalents of an iodine-containing cocatalyst at a temperature of ambient to about 100° C.

20 Claims, No Drawings

CHLORINATION AND BROMINATION OF AROMATIC COMPOUNDS AT ATMOSPHERIC PRESSURE

CROSS-REFERENCE TO RELATED APPLICATION

This patent application is related to application Ser. No. 09/412,672, filed Oct. 5, 1999 by Michael C. Savidakis and David C. Johnson titled, "Pressurized Chlorination and Bromination of Aromatic Compounds."

BACKGROUND OF THE INVENTION

This invention relates to a method of chlorinating and brominating aromatic compounds. In particular, it relates to a method of chlorinating and brominating aromatic compounds using a catalytic amount of a Lewis acid catalyst and about 0.001 to about 0.1 equivalents of an iodine cocatalyst at atmospheric pressure.

Aromatic compounds, such as methyl-4-methylbenzoate (M4MB), are commonly chlorinated at atmospheric pressure using chlorine gas in the presence of a Lewis acid catalyst, such as aluminum chloride, $AlCl_3$, or ferric chloride, $FeCl_3$. The amount of Lewis acid catalyst used must be greater than stoichiometric to effect the chlorination. For example, 0.98 lbs. (1.1 equivalents) of aluminum chloride are required to chlorinate each pound of M4MB.

If a weak Lewis acid is used, such as $FeCl_3$, chlorination will stop after the addition of one chlorine atom. If further chlorination is desired, more vigorous conditions, such as a higher temperature and/or pressure, are required. These conditions tend to lead to decomposition and the formation of undesired side products.

After the reaction is complete, separation of the catalyst from the product by filtration or distillation is impractical or not possible because the catalyst is chemically bound to the product. The usual procedure is to add water, causing the catalyst to react with the water to form a soluble product. For example, an aluminum chloride catalyst reacts with water to form hydrochloric acid and aluminum hydroxide, which dissolve in the water and can be separated from the solid product.

SUMMARY OF THE INVENTION

We have discovered that an aromatic compound can be chlorinated or brominated at atmospheric pressure using a catalytic amount of a Lewis acid catalyst and about 0.001 to about 0.1 equivalents of an iodine cocatalyst. As a result, we not only drastically reduce the amount of catalyst used, which reduces the amount of waste that must be processed and disposed of, but we do not require pressurized equipment.

The work-up with water is also eliminated. Instead, the catalyst can be removed by filtration, using a filter material with an affinity for the catalyst, a procedure that is not practical when a stoichiometric amount of catalyst is used. Alternatively, the product mixture can be distilled, which separates the desired product from the complex of the catalyst and product. Only a small amount of product is lost, compared to the large amounts of product lost if a stoichiometric amount of catalyst is used.

DESCRIPTION OF THE PREFERRED EMBODIMENTS

The substrates to be chlorinated or brominated can be any compound having an aromatic ring with at least one site available (i.e., a hydrogen atom) and at least one electron-withdrawing group on that ring. Preferably, the compound has 1 to 3 cojoined aromatic rings with 1 or 2 electron-withdrawing groups on each ring to be chlorinated; more electron-withdrawing groups on a ring may deactivate the ring and require more rigorous conditions. Types of aromatic compounds that can be used include benzoates, benzotrihalides, halogenated aromatics, acetophenones, and benzophenones; benzoates are preferred as they are economically important. Preferred aromatic compounds have the general formula

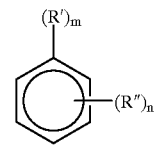

where each R' is an electron-withdrawing group independently selected from carboxylate, keto, trihalomethyl, and nitrilo, each R" is independently selected from R and OR, R is alkyl from $C_1$ to $C_{18}$, m is 1 or 2, and n is 0 to 5−m. Preferably, R' is ester, R" is R, R is alkyl from $C_1$ to $C_6$, m is 1 and n is 1 as those compounds are more important. Examples of particular aromatic compounds that can be chlorinated or brominated using this invention include methyl-4-methylbenzoate, methyl-3-methylbenzoate, methyl-3-chloro-4-methylbenzoate, p-chlorobenzonitrile, benzotrifluoride, parachlorobenzotrifluoride, benzotrichloride, parachlorobenzotrichloride, 2-chloronaphthalene, and 3'-chloroanthracene.

Any Lewis acid catalyst can be used, including aluminum chloride, ferric chloride, antimony (III) chloride, lead (IV) chloride, molybdenum (VI) chloride, thallium (I) chloride, tin (IV) chloride, titanium (IV) chloride, tungsten (VI) chloride, zirconium (IV) chloride, and mixtures thereof. The preferred Lewis acid catalyst is ferric chloride as it is inexpensive, easily removed from the product mixture, and environmentally friendly. About 0.1 to about 10 mole % (based on the aromatic compound) of the Lewis acid catalyst can be used; less is less effective and requires a long reaction time and more is unnecessary and offers no additional advantage. The preferred amount of Lewis acid catalyst is about 0.5 to about 5 mole %.

An iodine-containing cocatalyst is used in this reaction. Examples of suitable cocatalysts include iodine, ICl, $ICl_3$, alkali metal iodides, such as sodium iodide or potassium iodide, alkaline earth metal iodides, such as calcium iodide or magnesium iodide, alkyl iodides, where the alkyl group has 1 to 18 carbon atoms and preferably 1 to 6 carbon atoms, such as methyl iodide or ethyl iodide, and aryl iodides, where the aryl group contains 6 to 18 carbon atoms and preferably 6 to 10 carbon atoms, such as phenyl iodide. The preferred cocatalyst is iodine because it is inexpensive, does not form byproducts, and is easy to use as a solid or in solution. About 0.001 to about 0.1 equivalents of the cocatalyst should be used as less in ineffective and more is unnecessary. The preferred amount of cocatalyst is about 0.005 to about 0.06 equivalents.

Examples of chlorinating and brominating agents include chlorine gas, liquid bromine, BrCl, $SO_2Cl_2$, $SOCl_2$, $COCl_2$, $C_2O_2Cl_4$, $C_3O_3Cl_6$, n-chlorosuccinimide, n-bromosuccinimide, and 1,3-dibromo-5,5-dimethylhydantoin. Preferably, the chlorinating agent is chlorine gas and the brominating agent is liquid bromine as they effective and easier to use. About 1 to about 3 equivalents of chlorinating agent or brominating agent should be used for each chlorine or bromine atom to be added to the aromatic ring. Chlorination is preferred to bromination as it is commercially more important.

It is preferable to perform the reaction without a solvent in order to maximize throughput. However, if the desired product is a solid, it may be desirable to use about 5 to about 50 wt % of a solvent such as methylene chloride, chloroform, or dichloroethane to facilitate separation of the product.

The reaction can be performed at a temperature from about ambient to about 100° C.; at lower temperatures the reaction is slower and at higher temperatures byproducts may form. The preferred temperature range is about 40 to about 75° C.

The general procedure for the reaction is to charge a reactor with all the substrate, all the catalyst and cocatalyst, and some of the chlorinating agent or brominating agent and heat the mixture. Additional chlorinating or brominating agent is added as needed. The reaction is performed at atmospheric pressure. The products can be separated by distillation, filtration, or other means. The chlorinated and brominated aromatics can be used as chemical intermediates to make pharmaceuticals, agricultural chemicals, and other products.

The following examples further illustrated this invention. In these examples, EDC is ethylene dichloride, I is methyl-3-chloro-4-methylbenzoate, II is methyl-3,5-dichloro-4-methylbenzoate, III is methyl-2,5-dichloro-4-methylbenzoate, IV is methyl-2,3-dichloro-4-methylbenzoate, and V is methyl-2,3,5-trichloro-4-methylbenzoate.

EXAMPLES 1 to 7

The following tables gives the conditions and results:

| Example | M4MB (g) | $FeCl_3$ (equiv) | $I_2$ (equiv) | EDC (wt %) | Temp. (° C.) | Time (hr) | I (%) | II (%) | III (%) | IV (%) | V (%) | Other (%) |
|---|---|---|---|---|---|---|---|---|---|---|---|---|
| 1* | 3700 | 0.025 | 0 | 0 | 30–60 | 21 | 97.1 | 1.1 | 0.8 | 0.4 | 0.0 | 0.6 |
| 2 | 600 | 0.001 | 0.004 | 33 | 30 | 8 | 2.3 | 28.1 | 20.1 | 0.4 | 48.1 | 1.0 |
| 3 | 600 | 0.001 | 0.004 | 25 | 30 | 7 | 5.8 | 33.7 | 22.8 | 0.7 | 36.1 | 0.9 |
| 4 | 600 | 0.001 | 0.006 | 33 | 30 | 6 | 3.3 | 27.0 | 20.5 | 0.3 | 48.3 | 0.6 |
| 5 | 600 | 0.001 | 0.01 | 33 | 30 | 16 | 5.3 | 33.9 | 22.3 | 0.7 | 37.0 | 0.8 |
| 6 | 600 | 0.0002 | 0.01 | 25 | 30 | 27 | 6.1 | 36.3 | 22.3 | 0.6 | 33.8 | 0.9 |
| 7 | 600 | 0.0005 | 0.015 | 33 | 30 | 14 | 4.5 | 32.7 | 22.4 | 0.6 | 39.0 | 0.8 |

*Comparative

The above experiments show that significant dichlorination did not occur when no iodine-containing catalyst was used.

EXAMPLES 8 to 16

Examples 1 to 7 were repeated using 30 g of methyl-3-chloro-4-methylbenzoate, 25 wt % EDC, and a temperature of 40° C. The following tables gives the conditions and results:

| Example | $FeCl_3$ (equiv) | $I_2$ (equiv) | Time (hrs) | I (%) | II (%) | III (%) | IV (%) | V (%) | Other (%) |
|---|---|---|---|---|---|---|---|---|---|
| 8* | 0.001 | 0 | 7 | 96.1 | 2.1 | 1.1 | 0.3 | 0.0 | 0.4 |
| 9 | 0.001 | 0.0004 | 7 | 85.4 | 8.9 | 4.4 | 0.8 | 0.3 | 0.2 |
| 10 | 0.001 | 0.0020 | 7 | 46.9 | 29.0 | 16.7 | 1.8 | 5.4 | 0.2 |
| 11 | 0.003 | 0.0100 | 7 | 91.5 | 4.9 | 2.6 | 0.6 | 0.1 | 0.3 |
| 12 | 0.003 | 0.0010 | 7 | 64.0 | 19.2 | 12.4 | 1.8 | 2.4 | 0.2 |
| 13 | 0.003 | 0.0060 | 5 | 5.7 | 33.6 | 23.2 | 0.6 | 36.8 | 0.1 |
| 14 | 0.005 | 0.0020 | 7 | 86.1 | 8.1 | 4.4 | 1.0 | 0.3 | 0.1 |
| 15 | 0.005 | 0.0100 | 7 | 40.5 | 31 | 19 | 2.2 | 7.3 | 0.0 |
| 16 | 0.005 | 0.0500 | 3 | 7.2 | 32.6 | 24.4 | 0.9 | 34.8 | 0.1 |

*Comparative

The above experiments show that the rate of chlorination of I is very low when extremely low levels (0.001 equiv.) Of $FeCl_3$ are employed. They also show that acceptable rates can be obtained when 0.003 to 0.005 equiv. of $FeCl_3$ are used if >0.002 equiv. of $I_2$ are also used.

EXAMPLE 17

Comparative

M4MB (3720 g) was chlorinated with chlorine using 2.49 mole % of $FeCl_3$ at atmospheric pressure. During the initial stages of the chlorination, the temperature was kept below 40° C. Solids began to form after 8.5 hr, however, necessitating an increase in temperature to 60° C. After 21.2 hr, the reaction mixture remained solid at 60° C. An analysis of a sample of the mixture by gas chromatography (GC) indicated that 94% of the M4MB had been chlorinated to give 98.2% methyl-3-chloro-4-methylbenzoate with small amounts of dichlorinated methyl-4-methylbenzoates along with side-chain chlorinated by-products.

EXAMPLE 18 to 23

In each of the following examples the amount of M4MB chlorinated was 600 g. These reactions were carried out in a jacketed 1L reactor with mechanical stirring. The solvent employed in these reactions was 1,2-dichloroethane (EDC) and the reaction temperature was maintained at 25 to 32° C. using a chiller. The following table gives the reaction conditions:

| Example | $FeCl_3$ (mole %) | $I_2$ (mole %) | EDC (wt %) | Temperature (° C.) | Time (hrs) |
|---------|-------------------|----------------|------------|---------------------|------------|
| 18 | 1.0 | 3.0 | 33 | 27–31 | 6 |
| 19 | 1.0 | 2.0 | 33 | 30–32 | 8 |
| 20 | 1.0 | 2.0 | 25 | 25–30 | 7 |
| 21 | 1.0 | 1.0 | 33 | 29–30 | 16 |
| 22 | 0.5 | 1.5 | 33 | 30–32 | 14 |
| 23 | 0.2 | 1.0 | 25 | 28–31 | 27 |

The following table gives the chlorinated ester product distribution:

| Example | I | II | III | IV | V |
|---------|-----|------|------|-----|------|
| 18 | 3.3 | 27.0 | 20.5 | 0.3 | 48.3 |
| 19 | 2.3 | 28.1 | 20.1 | 0.4 | 48.1 |
| 20 | 5.8 | 33.7 | 22.8 | 0.7 | 30.1 |
| 21 | 5.3 | 33.9 | 22.3 | 0.7 | 37.0 |
| 22 | 4.5 | 32.7 | 22.4 | 0.6 | 39.0 |
| 23 | 6.1 | 36.3 | 22.3 | 0.6 | 33.8 |

The above examples show that similar product distributions can be obtained using differing amounts of $FeCl_3$ and $I_2$ and that the appropriate reaction conditions can be chosen based on desired cycle time, heat transfer limitations, or other manufacturing parameters. However, the inclusion of both $FeCl_3$ and $I_2$ is paramount.

We claim:

1. A method of adding 1 to 4 chlorine or bromine atoms to the aromatic ring of a compound having the general formula

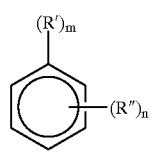

comprising reacting said compound with a chlorinating agent or a brominating agent in the presence of about 0.1 to about 10 mole % of a Lewis acid catalyst and about 0.001 to about 0.1 equivalents of an iodine-containing cocatalyst selected from the group consisting of inorganic iodides and alkyl iodides containing 1 to 18 carbon atoms at a temperature of ambient to about 100° C. and atmospheric pressure, where each R' is an electron-withdrawing group independently selected from carboxylate, keto, trihalomethyl, and nitrilo, each R" is independently selected from R and OR, R is alkyl from $C_1$ to $C_{18}$, m is 1 or 2, and n is 0 to 5–m.

2. A method according to claim 1 wherein said iodine-containing cocatalyst is selected from the group consisting of iodine, ICl, $ICl_3$, alkali metal iodides, and alkaline earth metal iodides.

3. A method according to claim 1 wherein said compound has 1 or 2 electron-withdrawing groups on said aromatic ring.

4. A method according to claim 1 wherein said electron-withdrawing group is a keto group.

5. A method according to claim 1 wherein said electron-withdrawing group is a nitrilo group.

6. A method according to claim 1 wherein said electron-withdrawing group is a carboxylate group.

7. A method according to claim 1 wherein said electron-withdrawing group is a trihalomethyl group.

8. A method according to claim 1 wherein said compound is a benzoate.

9. A method according to claim 8 wherein said benzoate is methyl-4-methyl benzoate.

10. A method according to claim 1 wherein said Lewis acid is ferric chloride.

11. A method according to claim 1 wherein said iodine-containing cocatalyst is iodine.

12. A method according to claim 1 wherein a chlorinating agent is used in said reaction.

13. A method according to claim 12 wherein said chlorinating agent is chlorine gas.

14. A method according to claim 1 wherein the amount of said chlorine gas is about 1 to about 3 equivalents per chlorine atom to be added to said aromatic ring.

15. A method according to claim 1 including the additional last step of passing the product mixture through a filter that has an affinity for said Lewis acid catalyst.

16. A method of adding 1 to 3 chlorine atoms to the ring of a compound having the general formula

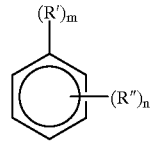

comprising (A) charging a reactor with said compound, about 0.5 to about 5 mole % of a Lewis acid, and about 0.005 to about 0.06 equivalents of an iodine-containing cocatalyst selected from the group consisting of iodine, ICl, $ICl_3$, alkali metal iodides, and alkaline earth metal iodides; and (B) adding about 1 to about 3 equivalents of chlorine gas to said reactor per chlorine atom to be added to said ring; and (C) heating said reactor to a temperature of about 40 to about 75° C., where each R' is independently selected from an carboxylate, keto, trihalomethyl, and nitrilo, each R" is independently selected from R or OR, R is alkyl from $C_1$ to $C_6$, m is 1 or 2, and n is 0 to 5–m.

17. A method according to claim 16 wherein said Lewis acid is ferric chloride.

18. A method according to claim 16 wherein said cocatalyst is iodine.

19. A method according to claim 16 wherein said compound is a benzoate.

20. A method of adding 1 to 3 chlorine atoms to the aromatic ring of methyl-4-methylbenzoate comprising (A) placing in a reactor
  (1) methyl-4-methylbenzoate;
  (2) about 0.5 to about 5 mole % ferric chloride;
  (3) about 0.005 to about 0.6 equivalents of iodine; and
  (4) about 1 to about 3 equivalents of chlorine gas per chlorine atom to be added to the ring of said aromatic ring; and (B) heating said autoclave to a temperature of about 40 to about 75° C.

* * * * *